United States Patent [19]
Biesert et al.

[11] Patent Number: 6,136,865
[45] Date of Patent: Oct. 24, 2000

[54] METHOD FOR REDUCTION OF THE INFECTIOUSNESS OF POTENTIALLY INFECTIOUS MATERIAL

[75] Inventors: Lothar Biesert, Offenbach; Horst Schwinn, Marburg; Wolfgang Marguerre, Heidelberg, all of Germany

[73] Assignee: Octapharma AG, Lachen, Switzerland

[21] Appl. No.: 08/472,776

[22] Filed: Jun. 7, 1995

[30] Foreign Application Priority Data

May 20, 1995 [EP] European Pat. Off. ............ 95107710

[51] Int. Cl.[7] .................... A61K 31/075; A61K 31/20
[52] U.S. Cl. .................. 514/718; 514/558; 514/559; 514/560; 514/720
[58] Field of Search .................... 514/718, 558, 514/559, 560, 720

[56] References Cited

U.S. PATENT DOCUMENTS 5,385,733   1/1995   Monkouts ........................ 424/195.1

FOREIGN PATENT DOCUMENTS

| | | |
|---|---|---|
| 0 112 563 | 7/1984 | European Pat. Off. . |
| 0 239 859 | 10/1987 | European Pat. Off. . |
| 0525502A1 | 7/1992 | European Pat. Off. . |
| 4021542A1 | 1/1992 | Germany . |
| WOA8304371 | 12/1983 | WIPO . |
| 94117834 | 8/1994 | WIPO ............... A61L 2/04 |
| WOA9417834 | 8/1994 | WIPO . |

OTHER PUBLICATIONS

Revici et al 103CA:11486j 1985.
Brodley et al 116CA: 28234S 1992.
Asculai et al Antimro & Chemaltys 1978, U61 13(4) pp 686–690.
Polsky et al. 1988, Lancet, Jun. 25.
Field's Virology 3rd Ed Fields ed 1996, pp 2705, 2727–29.
Field et al, Field's Virology, Lippincot–Rover, Phil PA P25.
Davis et al, Microbiolgy, Hoper & Row pp 1462–64, 1970.
La Torre et al, 98 CA 1855510, 1983.
Bondarenko et al 87CA; 96740m, 1977.
Sharma 118CA: 668325, 1993.
Bradley et al 116CA 28234s, 1991.
Copy of European Search Report, Oct. 9, 1995.

*Primary Examiner*—Kevin E. Weddington
*Attorney, Agent, or Firm*—Jacobson, Price, Holman & Stern, PLLC

[57] ABSTRACT

A method for reduction of the viral infectiousness of potentially infectious material, such as human or animal body fluids or fractions derived therefrom from which biologically active substances can be isolated, wherein the infectiousness is due to non-lipid-coated viruses characterized in that said potentially infectious material for the isolation of said biologically active substances is treated with a hydrophobic phase which is essentially insoluble in water and is capable of forming a two-phase system with said potentially infectious material, and said hydrophobic phase is separated from the potentially infectious material thus treated.

14 Claims, No Drawings

METHOD FOR REDUCTION OF THE INFECTIOUSNESS OF POTENTIALLY INFECTIOUS MATERIAL

The object of the present invention is a method for reduction of the viral infectiousness of potentially infectious material, such as human or animal body fluids or fractions derived therefrom from which biologically active substances can be isolated, wherein the infectiousness is due to non-lipid-coated viruses.

Potentially infectious materials, such as human or animal body fluids, are an important pool of biologically active and hence valuable substances. However, isolation of the biologically active substances from these sources is not unproblematic which has become apparent in the past especially in the case of HIV transmission by preparations recovered from blood plasma. Thus, an essential requirement for the administration of such preparations is their being virus-proof, i.e. no infectious particles must be transmitted with these preparations.

Viruses which are lipid-coated are effectively inactivated by treatment with non-ionic biocompatible solvents and detergents. Such methods are described in EP 0 131 740. Non-lipid-coated viruses are not adequately inactivated by such treatment. WO 94/17834 reports that an adequate inactivation of non-lipid-coated viruses, such as hepatitis A viruses, for instance, is achieved only by combined treatment of a solution by non-ionic detergents and heating thereof at 60 to 65° C. However, the heat treatment period being as long as more than 5 to 30 hours represents a drawback since the valuable biologically active substances are predominantly proteins, the complex structure of which is altered or even destroyed by such heat treatment. This involves reduction of the activity of the corresponding fractions. Thus, the known methods result in a reduction of the potential recovery of these products.

Thus, the problem underlying the invention is to provide a method by which a reduction of the infectiousness of non-lipid-coated viruses contained in potentially infectious or actually infectious materials can be achieved.

Surprisingly, it has been shown that infectiousness due to non-lipid-coated viruses in potentially infectious materials can be reduced by treatment of such materials with a hydrophobic phase capable of forming a two-phase system with said potentially infectious material and separation of the phases formed.

The method according to the invention for reduction of the viral infectiousness of potentially infectious material, such as human or animal body fluids or fractions derived therefrom from which biologically active substances can be isolated, wherein the infectiousness is due to non-lipid-coated viruses is characterized by the following measures. The potentially infectious material for the isolation of the biologically active substances is treated with a hydrophobic phase which is essentially insoluble in water and will form a two-phase system with said potentially infectious material. Thereafter, the hydrophobic phase is separated from the potentially infectious material thus treated.

In the following, by a potentially infectious material is also meant actually infectious material. In particular, this includes body fluids such as blood or blood plasma or processed blood or blood plasma, such as cryoprecipitate. In addition, however, this includes any fractions of such potentially infectious materials as well as cell lysates or similar natural sources.

The biologically active substances which can be isolated from the potentially infectious material are, in particular, proteins, such as factors of the blood-clotting cascade, such as factor VIII or vitamin K dependent factors, such as the C and S proteins, gamma-globulins, complementary factors, and serin protease inhibitors.

In particular, the hydrophobic phase capable of forming a two-phase system with the potentially infectious material which can be employed according to the invention is a non-polar organic liquid, such as a liquid which is an oil at room temperature, such as vegetable oil, or low-melting fats.

Not only is the method according to the invention compatible with existing methods for virus inactivation by means of non-ionic detergents and dialkyl or trialkyl phosphates, but it has proven a further advantage to complement the hydrophobic phase treatment of the potentially infectious material with a treatment with non-ionic detergents and dialkyl or trialkyl phosphates, especially tri-n-butyl phosphate (TNBP). This combined treatment can be performed simultaneously or sequentially.

The following derivatives may be mentioned as non-ionic detergents, which should be present in amounts of at least 0.1% by weight: bile salts, polyoxyethylene derivatives of fatty acids, partial esters of sorbitol anhydride, e.g. products traded under the designations of Tween 80, Tween 20 and Polysorbat 80, as well as non-ionic, oil-soluble surfactants, especially those known by the trade name of Triton X-100 (ethoxylated alkylphenols). Also possible are zwitterionic reagents, for example, sulfobetains, such as N-dodecyl-N,N-dimethyl-2-ammonio-1-ethanesulfonate or derivatives thereof, or non-ionic detergents, such as octyl-β-D-glucopyranosides. The amount of detergents is preferred to be from 0.01% to 10%. Preferred treatments involve combinations of TNBP, Tween and Triton, or sodium cholate/TNBP.

The treatment of the potentially infectious material with the hydrophobic phase is quasi substituted for the heat treatment step required in WO 94/17834 which, in combination with non-ionic detergents and alkyl phosphates, inactivates the non-lipid-coated viruses.

Possible non-lipid-coated viruses are in particular hepatitis A, coxsackie, polio and parvo viruses.

The method according to the invention is effective especially in the case that the hydrophobic phase is intimately mixed with the potentially infectious material. This can be achieved, for instance, by mechanical action, such as ultrasonic treatment, high-performance stirring, intense agitation etc.

After the two-phase system has been formed, the hydrophobic phase can be removed, in particular, by centrifugation or filtration. As the hydrophobic phase, there may be used, in particular, vegetable oils, such as soybean oil and/or castor oil. The oily phase can be removed by filtration through a hydrophobic filter. The degree of separation of the hydrophobic phase required primarily depends on the subsequent further processing. If the materials reduced in infectiousness by non-lipid-coated viruses are further purified, for example, by anion-exchange or affinity chromatography, then quantitative separation of the hydrophobic phase is not required. Therefore, it should be ensured that the infectious particles which may have been extracted into the hydrophobic phase are separated off. However, if a quantitative elimination of the hydrophobic phase is essential, said phase may be removed in a manner analogous to that described in DE 40 08 852. As separation procedures, the separation procedures common in biochemistry may be used, including electrophoresis.

The method according to the invention is excellently suitable for the isolation of biologically active substances, such as factors of the blood-clotting cascade, for example, factor VIII, vitamin K dependent clotting factors, etc.

The invention will be further illustrated by the following example.

EXAMPLE

To a potentially infectious blood plasma fraction, viruses are added which are not lipid-coated. The respective virus levels can be seen from the table. As non-coated viruses, coxsackie B6 and polio 1 were employed. Lipid-coated PRV virus is used as a control. Experiments have been performed with the non-lipid-coated viruses involving treatment with non-ionic detergents and TNBP (SD) or no such treatment ((−) in the SD column of the table). The sample is treated with oil.

To portions of about 20 ml each of a blood plasma fraction (e.g. containing factor VIII), coxsackie, polio, or pseudorabies viruses are added to the levels of infectious virus given in the table.

Subsequently, with intense stirring, 1. 0.2 ml of Tween 80 and 0.06 ml of TNBP are added to 19.74 ml of the fraction, or
2. 0.2 ml of Triton X-100 and 0.2 ml of TNBP are added to 19.6 ml of the fraction.
1 ml each of castor oil is added to preparations 1 and 2 which are then intensely extracted at room temperature for one hour.
3. Another 20 ml of the virus-containing fraction is treated immediately with 1 ml of castor oil in the above manner without prior treatment with detergents (SD-).

Centrifugation is performed in each case for phase separation. For infectiousness control, samples of 1 ml each are repeatedly taken from the aqueous fraction.

| virus | SD | level before* | level after* | level reduction |
|---|---|---|---|---|
| PRV | − | 6.84 ± 0.32 | 6.18 ± 0.30 | 0.66 ± 0.62 |
| coxsackie B6 | + | 6.96 ± 0.32 | 2.79 ± 0.17 | 4.17 ± 0.49 |
| | − | 6.78 ± 0.23 | 3.56 ± 0.32 | 3.22 ± 0.55 |
| polio 1 | + | 7.02 ± 0.38 | <2.73 ± 0.12 | >4.29 ± 0.50 |
| | − | 6.90 ± 0.32 | 4.16 ± 0.28 | 2.74 ± 0.60 |

*$\log_{10}$ TCID$_{50}$ per ml

What is claimed is:

1. A method for inactivating non-lipid-coated virus contained in material from a human or animal comprising the steps of:

treating the material with a water-insoluble hydrophobic phase, which forms a two-phase system with the material; and separating the hydrophobic phase from the material in two-phase system.

2. The method according to claim 1, wherein the material is blood, blood plasma, processed blood, or processed blood plasma.

3. The method according to claim 2, wherein the material is a blood cryoprecipitate.

4. The method according to claim 1, further comprising the step of recovering from the separated material a biologically active substance.

5. The method according to claim 4, wherein the biologically active substance is a protein.

6. The method according to claim 5, wherein the protein is a factor of the blood-clotting cascade.

7. The method according to claim 1, wherein the water-insoluble hydrophobic phase includes non-polar organic liquids.

8. The method according to claim 7, wherein the non-polar organic liquids are oils at room temperature or low-melting fats.

9. The method according to claim 1, further comprising the step of, either simultaneously with or sequentially to treating the material with the water-insoluble hydrophobic phase, treating the material with a non-ionic detergent and an alkyl phosphate.

10. The method according to claim 9, wherein the alkyl phosphate is tri-n-butyl phosphate, and the non-ionic detergent is a polyether.

11. The method according to claim 1, further comprising the step of, sequentially to separating the hydrophobic phase from the two-phase system, fractionating the separated material into separate fractions.

12. The method according to claim 11, wherein fractionating is performed by affinity chromatography, ion-exchange chromatography, electrophoresis, gel-permeation chromatography, or hydrophobic reversed phase chromatography.

13. The method according to claim 11, further comprising the step of recovering at least one biologically active substance from one or more of said fractions.

14. The method according to claim 10, wherein the polyether is a TRITON derivative.

* * * * *